(12) United States Patent
Wimberger-Friedl et al.

(10) Patent No.: US 9,823,196 B2
(45) Date of Patent: Nov. 21, 2017

(54) DNA SEQUENCING WITH REAGENT RECYCLING ON WIREGRID

(71) Applicant: KONINKLIJKE PHILIPS N.V., Eindhoven (NL)

(72) Inventors: Reinhold Wimberger-Friedl, Eindhoven (NL); Johan Lub, Eindhoven (NL); Pieter Jan Van Der Zaag, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 95 days.

(21) Appl. No.: 14/371,890

(22) PCT Filed: Jan. 9, 2013

(86) PCT No.: PCT/IB2013/050168
§ 371 (c)(1),
(2) Date: Oct. 23, 2014

(87) PCT Pub. No.: WO2013/105025
PCT Pub. Date: Jul. 18, 2013

(65) Prior Publication Data
US 2015/0079585 A1    Mar. 19, 2015

Related U.S. Application Data

(60) Provisional application No. 61/586,260, filed on Jan. 13, 2012.

(51) Int. Cl.
*C12M 1/34* (2006.01)
*G01N 21/64* (2006.01)
*C12Q 1/68* (2006.01)

(52) U.S. Cl.
CPC ....... *G01N 21/6486* (2013.01); *C12Q 1/6874* (2013.01); *G01N 21/648* (2013.01);
(Continued)

(58) Field of Classification Search
CPC ...... G01N 21/4792; G01N 21/64; C12M 1/00
See application file for complete search history.

(56) References Cited

U.S. PATENT DOCUMENTS 6,391,560 B1 *  5/2002  Schmidt ............... B01L 3/5027
                                                          422/50
7,170,050 B2   1/2007  Turner et al.
(Continued)

FOREIGN PATENT DOCUMENTS

EP      2221605 A1      8/2010
NL   WO2010/029498   *  3/2010
(Continued)

OTHER PUBLICATIONS

Eid, J. et al., "Real-Time DNA Sequencing from Single Polymerase Molecules", Science, vol. 323, Jan. 2009, pp. 133-138, www.sciencemag.org/cgi/content/full/1162986/DC1.
(Continued)

*Primary Examiner* — Narayan Bhat

(57) ABSTRACT

The present invention relates to DNA sequencing with reagent cycling on the wiregrid. The sequencing approach suggested with which allows to use a single fluid with no washing steps. Based on strong optical confinement and of excitation light and of cleavage light, the sequencing reaction can be read-out without washing the surface. Stepwise sequencing is achieved by using nucleotides with optically cleavable blocking moietys. After read-out the built in nucleotide is deblocked by cleavage light through the same substrate. This ensures that only bound nucleotides will be unblocked.

18 Claims, 9 Drawing Sheets

(52) U.S. Cl.
CPC ..... *G01N 21/6428* (2013.01); *G01N 21/6458* (2013.01); *B01J 2219/00576* (2013.01); *B01J 2219/00605* (2013.01); *B01J 2219/00711* (2013.01); *B01J 2219/00722* (2013.01); *G01N 2021/6439* (2013.01); *G01N 2201/06113* (2013.01); *G01N 2201/103* (2013.01)

(56) References Cited

U.S. PATENT DOCUMENTS

| | | |
|---|---|---|
| 7,897,737 B2 | 3/2011 | Wu et al. |
| 8,747,751 B2 | 6/2014 | Duer et al. |
| 2008/0132692 A1* | 6/2008 | Wu .......... C07H 21/04 536/25.3 |
| 2009/0181381 A1* | 7/2009 | Oldham .......... C12Q 1/6825 435/6.11 |
| 2009/0312188 A1* | 12/2009 | Duer .......... G02B 27/56 506/6 |
| 2010/0252751 A1 | 10/2010 | Klunder et al. |
| 2010/0320363 A1 | 12/2010 | Schleipen |
| 2010/0331194 A1 | 12/2010 | Turner et al. |
| 2011/0117637 A1* | 5/2011 | Gray .......... G01N 21/6452 435/287.2 |

FOREIGN PATENT DOCUMENTS

| | | |
|---|---|---|
| WO | WO2006007207 A2 | 1/2006 |
| WO | WO2006044078 A2 | 4/2006 |
| WO | 2008070749 A2 | 6/2008 |
| WO | WO2009060360 A2 | 5/2009 |
| WO | WO2009107041 A1 | 9/2009 |

OTHER PUBLICATIONS

Metzker, M.L., "Sequencing Technologies—the Next Generation", Nature Reviews/Genetics, vol. 11, Jan. 2010, pp. 31-46, www.nature.com/reviews/genetics.

Litosh, V.A. et al., "Improved Nucleotide Selectivity and Termination of 3'-OH Unblocked Terminators by Molecular Tuning of 2-Nitrobenzyl Alkylated HOMedU Triphosphates", Nucleic Acids Research, .2011, vol. 39, No. 6.

Levine et al "Real-Time Multiplelxed Electrochemical DNA Detection Using an Active Complementary Metal-Oxide-Semiconductor Biosensor Array With Integrated Sensor Electronics" Biosens Bioelectron 2009 Mar. 15, 2010, p. 1995-2001.

M.R. Schmidt "The Wire Grid Biosensor for Nucleic Acid Testing" Technical Note Philips Research Europe Jun. 2009.

\* cited by examiner

DNA SEQUENCING WITH REAGENT RECYCLING ON WIREGRID

CROSS-REFERENCE TO RELATED APPLICATIONS

This patent application claims the priority benefit under 35 U.S.C. §371 of international patent application no. PCT/IB2013/00168, filed Jan. 9, 2013, which claims the priority benefit under 35U.S.C. §119(e) of U.S. Provisional Application No. 61/586,260 filed on Jan. 13, 2012, the contents of which are herein incorporated by reference.

FIELD OF THE INVENTION

The present invention relates to the determination of the sequence of nucleic acid. In particular, the present invention relates to a device for optically controlling an iterative stepwise reaction to determine a sequence of a nucleic acid, a method for optically controlling an iterative stepwise reaction to determine a sequence of nucleic acid, a program element, a computer-readable medium on which a program element is stored and the use of a moiety as a blocking moiety in DNA sequencing.

BACKGROUND OF THE INVENTION

DNA sequencing is a rapidly developing field with key players such as Illumina (using the Solexa technology), Life (using the Solid technology) and Roche Diagnostics (using the 454 technology). The drawback of the sequencing methods these companies use is that the sequence information is obtained by a repetition of several steps which involve replacing reagents and washing. This is cumbersome and time consuming and wastes a lot of expensive reagents. The number of repetitions is equal to the number of nucleotides that are interrogated, i.e. the read length. With the desire to increase read length this problem will become more severe in the future. Currently, this is compensated by highly parallel sequencing on large arrays. However, for clinical applications this is less desirable. One would rather have a fast answer and a lower multiplexing. At the same time the cost per base pair has to come down significantly. Since after every step, i.e. after nucleotide incorporation, the whole surface needs to be washed, all reagents end up in the waste. The total reagent consumption is proportional to the read length and the dominant cost factor of sequencing at the moment.

The process of sequencing a particular target, such as e.g. DNA becomes more complex, since the incorporation reaction needs to be followed by an activation reaction and in between careful washing steps are required.

Alternative approaches, like that of Pacific Biosciences are more efficient as they follow the incorporation of nucleotides in real time for every molecule separately. In this way no washing is required. The optical requirements for such a system on the other hand are very severe, as one needs single fluorophore sensitivity for 4 different colors in real time. This can only be achieved for a limited area as the field of the objective lenses with high magnification is limited for practical systems and a strong laser light source. With the limited area only a small selection of a sample can be sequenced and the risk of errors due to missed reads is high. The fluorescent signals from labeled nucleotides while they are built in by the polymerase need to be discriminated from those of the same kind of molecules which happen to be at the same position by chance. This is done by analyzing the pulse length of the fluorescence signal.

SUMMARY OF THE INVENTION

There may be a need to provide an improved determination of the sequence of a nucleic acid. The present invention matches this need.

The object of the present invention may be seen as to provide for an improved determination of a sequence of a nucleic acid.

The object of the present invention is solved by the subject-matter of the independent claims. Further embodiments and advantages of the invention are incorporated in the dependent claims.

It shall be noted that the herein described embodiments similarly pertain to the method for optically controlling an iterative stepwise reaction to determine a sequence of a nucleic acid, the device for optically controlling an iterative stepwise reaction to determine the sequence of the nucleic acid, the computer program element, the computer-readable medium and the use of a moiety as a blocking moiety in DNA sequencing. Synergistic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. All different orders and combinations of the method steps are herewith described.

In the context of the present invention, the term "blocking moiety" is to be understood as a moiety which blocks a synthesizing activity of an enzyme in the case where the blocking moiety is incorporated into a molecule at which the enzyme performs a synthesizing process. A blocking moiety may be e.g. a blocking molecule.

In the context of the present invention, the term "cleavable" should be understood as allowing to be cleaved away by absorbing cleavage light of wavelength $\lambda_{CL}$.

In the context of the present invention it should be understood, that every embodiment of the optical arrangement disclosed herein may be configured to emit polarized excitation light and polarized cleavage light. Thus, a polarizer or already polarized light sources may be used. Details will be described later on.

Furthermore, the term "excitation light" in the context of the present invention applies to the wavelength $\lambda_{Ex1}$, $\lambda_{Ex2}$, $\lambda_{Ex3}$ and $\lambda_{Ex4}$, respectively.

According to an exemplary embodiment of the invention, a device for optically controlling a DNA sequence is presented. In particular, the device is configured to optically control an iterative stepwise reaction to determine a sequence of a nucleic acid by synthesis. Alternatively, instead of sequencing by synthesis, a synthesis by ligation is also to be understood in the scope of the present invention. The presented device comprises a substrate for binding at least one molecule on a first surface of the substrate. The device further comprises an optical arrangement which is configured to direct excitation light of at least a first excitation wavelength $\lambda_{Ex1}$ to the substrate to excite a fluorescent label of a first nucleotide which is incorporated into the molecule that is bound on the first surface of the substrate. The optical arrangement is further configured to receive and detect fluorescent light emitted by the fluorescent label of the first nucleotide which is incorporated into the bound molecule. Furthermore, the optical arrangement is configured to direct cleavage light of a cleavage wavelength $\lambda_{CL}$, preferably UV light, to the substrate to optically induce a photochemical cleavage reaction at the first incorporated nucleotide to cleave a blocking moiety and the fluorescent label away from the first incorporated nucleotide. Furthermore, the substrate is configured to confine the excitation light and is configured to provide thus for an evanescent wave of the excitation light as the first surface of the substrate. Furthermore, the substrate is configured to confine the cleavage light, preferably UV light, and is further configured to provide for an evanescent wave of cleavage light at the first surface of the substrate.

Here a device is proposed which is able to combine the advantages of known sequencing devices. The devices allows for ensemble based easy read out but no or a reduced number of washing steps is required, meaning a single reagent filling for all reads.

In other words, a sequencing device is presented by the present invention, which allows to carry the sequencing out in a single fluid and in which no or a reduced number of washing steps is required. The required reagent volume, i.e. costs, is reduced by a factor equal to the read length (50-100). Based on the strong confinement of the excitation light on the substrate, i.e. a nano-photonic surface structure like a wiregrid, the sequencing reaction can be read-out without washing the surface. Total internal reflection may also be used in order to provide the evanescent wave.

Stepwise sequencing is achieved by using nucleotides with optically cleavable blocking groups. After read-out, the built-in nucleotide is unblocked by cleavage light like for example UV radiation through the same nano-photonic substrate. This ensures that only bound nucleotides will be unblocked. The cost and speed of DNA sequencing is strongly related to reagent consumption. The speed and complexity of the sequencing work stations, instruments and cartridges, is largely determined by the necessity of fluid handling for repeating reaction and washing steps. Both aspects are improved by the present invention leading to a dramatic exemplification and cost reduction of sequencing.

As it will be explained in detail in the following, the optical arrangement may also be configured to direct excitation light of a first, and a second, and a third and a fourth excitation wavelength $\lambda_{Ex1}$, $\lambda_{Ex2}$, $\lambda_{Ex3}$ and $\lambda_{Ex4}$, to the substrate to excite a fluorescent label of a first nucleotide incorporated into a molecule bound on the first surface of the substrate. Thereby, it can be ensured that e.g. four different nucleotides, like for example Adenine (A) and Guanin (G) and Thymine (T) and Cytosine (C), can be distinguished, when the respective nucleotide uses a specific and differentiated fluorescent label. However, if desired, also only one or two or three of the four excitation wavelength $\lambda_{Ex1}$, $\lambda_{Ex2}$, $\lambda_{Ex3}$ and $\lambda_{Ex4}$ described above may be directed by the device towards the substrate to excite the molecule, i.e., the fluorescent label of a nucleotide which is incorporated in the bound molecule. Details about four color systems, in which four different fluorescent labels for the above described nucleotides A, G, C, and T are used will be explained hereinafter in more detail with respect to the following FIGS. 1 and 2. The bound molecule might be a DNA fragment and can be understood as the nucleic acid whose sequence of nucleotides is determined by the present invention.

Furthermore, a person skilled in the art of sequencing or DNA sequencing is aware of the fact that the wavelength $\lambda_{Ex1}$, $\lambda_{Ex2}$, $\lambda_{Ex3}$ and $\lambda_{Ex4}$ are chosen in combination with the four fluorescent labels used for, for example, a nucleotides A, G, C, and T. In other words, the wavelengths are chosen such that the used fluorescent labels, can be optically excited by the respected excitation light. Furthermore, the wavelength $\lambda_{CL}$ is chosen such that the desired cleaving reaction of the used nucleotides can be optically caused by irradiating said cleavage light.

As an exemplary embodiment, the following wavelength may be used, although the person skilled in the art may be part from the explicitly disclosed wavelength. The excitation wavelengths could be chosen based on the following: Optimal spacing of the excitation wavelengths over the visible spectrum and in agreement with absorption spectra of most commonly used dyes e.g. FAM, HEX, Cy3 Cy5, Alexa Fluor 700 or Atto700, or similar. The excitation wavelengths may also be adjusted to availability of light sources like e.g. solid-state laser light sources with e.g. 405, 532, 633 and 780 nm. However, the invention is not limited to said excitation wavelengths. The emission maximum of the respective dye may be chosen such that no overlap with the excitation wavelength of the neighboring occurs. Furthermore, the cleavage light, preferably UV light, may be in the range of 250-400 nm, preferably 300-370 nm. However, the invention is not limited to said excitation wavelengths.

It shall be noted that the molecule which is bound at the first surface of the substrate may for example be a DNA fragment, DNA, RNA, mRNA or another nucleic acid. Furthermore, also an enzyme, which will be described herein later on, may be bound to the first surface of the substrate. In the context of the present invention, the term "bound" shall be understood as a state in which the element is immobilized to the first surface of the substrate.

In addition, the substrate provides for spots which may be covered with clones of identical molecules, in order to increase the optical signal, which is received by detecting the fluorescence. Therefore, a substrate may be provided as an array of such spots with respectively different clones, such that throughput of sequencing is increased.

In other words, the above presented device of the present invention allows for an assembly-based optical sequencing process without washing steps, such that the total process of determining a sequence of a nucleic acid by synthesis can be carried out in a single solution on the substrate. The process steps can be controlled optically. The process of unblocking, which shall be understood in the present invention as activation, of the incorporated nucleotide can be carried out by the irradiation of a surface selective, evanescent radiation of cleavage light. Preferably, such irradiation is performed with UV light. The process is described as directing cleavage light of a cleavage wavelength $\lambda_{CL}$ to the substrate to optically induce the photochemical cleavage reaction at the first incorporated nucleotide. Therefore, the presented device is configured to cleave only the fluorescent label away from the first incorporated nucleotide by irradiating the substrate with an evanescent wave of cleavage light. Thus, only incorporated nucleotides will be unblocked, activated or cleaved due to the localization of the evanescent field of cleavage light. The same evanescent field illumination is used by the presented device for reading the fluorescence of the incorporated basis or nucleotides against the background of fluorescent labels in solution. The localization of the optical field of excitation light, which comprises at least the first excitation wavelength $\lambda_{Ex1}$, is achieved by the evanescent field of said excitation light.

For example, the evanescent wave of cleavage light and the evanescent wave of excitation light can be generated by the substrate of the presented device by providing for a wiregrid. This may allow for using a focused beam of high intensity such that the photo-optical reaction occurs at a high rate in a very limited area very close to the surface. The optical arrangement may comprise respective optical elements for the excitation and detection of fluorescence, i.e. the read-out, and respective optical elements for unblocking, i.e. activation, in a single optical arrangement unit or may also be comprised in physically differentiated elements.

Furthermore, the respective excitation light source may be comprised by the optical arrangement. Furthermore, the light source for emitting cleavage light may be comprised by the optical arrangement. Illumination for cleaving, i.e. unblocking and read-out, i.e. excitation and detection of fluorescence, can optionally occur through the same lens. However, if desired, also two different optical set-ups for unblocking and reading-out can be presented.

The evanescent wave field used in the present invention decays exponentially with distance from the first surface, with a decay length depending on the complex refractive index of the material, e.g. metal, of the wiregrid and that of the medium between the wires, under the condition that the aperture between the metal wires is smaller than the optical resolution at the pertinent wavelength. For example the aperture may be 70 nm which is well below that limit also for UV light. The decay length is estimated as 16.8 nm (see below), which means that the field has decreased to 1/e of the irradiated intensity at that distance from the interface of the metal wire and the substrate. This might be slightly different from the first surface due to underetching of the first surface between the wires.

In other words, the presented device provides for a surface selective cleavage light irradiation and a surface of excitation light irradiation. The substrate may be configured as a nano-photonic surface structure, such that the above described optical confinements of the excitation light and the cleavage light and additionally the evanescent waves of cleavage light and excitation light are generated. The combination of inter alia, the excitation light, i.e. the read-out optics, and the cleavage light allow for an iterative stepwise reaction to determine the sequence of nucleic acid by synthesis. This has the benefit that washing steps can be omitted. Subsequently, the steps and cycles described above which are performed with the presented device, can be repeated many times to allow for a stepwise incorporation of one or more further nucleotides into the bound molecule and afterwards reading out, whether said nucleotide has been incorporated or not as described above.

The device may be further configured to achieve data which describe the differences of the nucleic acids that were incorporated into the bound molecule based on the optically stepwise action that is controlled optically by the device.

Furthermore the substrate may be out of a polymer e.g. poly-(cyclo-)olefin, poly-carbonate, polyester or PMMA. Also metal and semiconductors may be used.

According to another exemplary embodiment of the invention, the device further comprises the molecule which is bound to the first surface of the substrate. The device further comprises a solution with a plurality of nucleotides and an enzyme. Therein, the nucleotides respectively comprise the blocking moiety. The blocking moiety is configured to block a synthesizing activity of the enzyme when the respective moiety is incorporated into the molecule bound to the first surface of the device.

If desired, the blocking moiety comprises the fluorescent label. However, the blocking moiety and the fluorescent label may be incorporated or positioned at the first nucleotide at different positions. They may be cleaved away in one single cleavage process or in different cleavage processes. This holds for every embodiment of the present invention.

The herein presented embodiment provides for the advantage that the reaction of incorporation stops on its own due to the comprised blocking moiety. For example, steric hindering can used by the blocking moiety to block the synthesizing activity of the enzyme. This allows doing a local read-out of a reaction that is occurring on many spots simultaneously. In the prior art the action of used enzymes in a sample in the device cannot be synchronized. However, the present invention allows for the incorporation of nucleotides, which can advantageously be done step by step together with a read-out after every step. The advantage is achieved by using the above-described blocking moieties, which may be blocking nucleotides, that block the activity of the enzyme after the nucleotide is incorporated. Active unblocking is required to continue with the incorporation of the next nucleotide, which the present invention allows by the optical arrangement that is configured to direct cleavage light to cleave away the blocking moiety. The blocking moiety may comprise the fluorescent label.

As exemplary embodiments, the blocking moieties may be embodied as 3'-blocked reversible terminator or as 3'-unblocked reversible terminator as described and defined in "*Sequencing technologies, the next generation*" by Michael L. Metzker, Nature Review Genetics 11 (2010) 31-46. Therein, also termed "unblocked", said blocking moieties 3'-unblocked reversible terminator can be used as blocking an activity of an enzyme. Reversible terminators may be understood as ligands attached to the nucleotide/ribose unit which stop the incorporation of any subsequent nucleotide after the incorporation. They are reversible when upon cleavage by chemical or photochemical means this process can be undone and the polymerase can build in the next nucleotide. Furthermore, the 3'-blocked reversible terminator of Metzker et al can be amended, for example chemically, to make them photo cleavable. Then, the photo cleavage with the cleavage light can be performed by means of the present invention. In addition, other complexes may be used as blocking moieties in combination with the respective enzyme as will be described later on. The skilled person knows, which combination of enzyme and blocking moiety leads to the desired effect of blocking the synthesizing activity of the enzyme.

The herein used terminology regarding said blocking moieties is in line with and adapted to the disclosure of said article. Said second class of moiety is of an additional advantage as is the case of the 3'-position of the ribose unit is unblocked and the incorporation of the next nucleotide is prevented by the bulky group that also contains the fluorescent label attached to the base pairing moiety at 5'-position of the ribose unit. This can also be gathered from the following FIG. 6 and its description. Propagation of the nucleotide oligomer is prevented as long as this group is attached. However, incorporation of the next nucleotide is enabled after removal of the bulky group. The present invention provides for such a removal by inducing a photochemical cleavage reaction. More advantageously, the present invention uses such cleavage reaction only very close to the surface at which the molecule is bound, due to the fact that an evanescent wave of cleavage light is generated.

In addition to the following description, the details about FIGS. 6, 8 and 10 should be taken into account, in which blocking moieties with comprised fluorescent label are disclosed.

According to another exemplary embodiment of the present invention, the blocking moiety is a photo-cleavable 3'-unblocked reversible terminator.

According to another exemplary embodiment, the blocking moiety is chosen from the group comprising a derivative of nitrophenylethyl, 5-methyl-(2-(2-nitrophenyl)propyl)carbonate-dUTP analogue, 5-methyl(2-oxo-1,2-diphenylethyl) carbonate-dUTP analogue, and any combinations thereof.

According to another exemplary embodiment, the substrate is configured as a wiregrid for the excitation light and for the cleavage light.

The wiregrid may comprise a pattern of metal wires on, for example, a glass substrate. The spacing between the wires acts as a metal-clad slab waveguide, in which the major contribution comes from two fundamental modes. For example, for TE polarized excitation light incident on the wires of the substrate of the present invention the resulting mode in between the wires is the evanescent mode, having an exemplary decay length of 16.8 manometers for λ=630 nanometer. Therein assuming the wires of the substrate are filled with a medium having a refractive index of water, n=1.33. For TM polarized light, the resulting mode for a wiregrid is called a propagating mode, having a decay length of 1.2 µm in this example. For example, the wire height may be 60 manometers in an example. Therein the TM polarized mode is transmitted with a loss of light in the order of 10% or less, while the TE polarized mode is evanescently decaying.

A different way to understand the wiregrid is to think of e.g. aluminium wires as metals which reflect excitation light with polarization parallel to the wires (TE polarization) and which transmit polarization orthogonal to the wires (TM polarization). The maximum transmission of TM polarized light may be higher than 95%. The evanescent field in the case of incident TE excitation light is depicted in both FIGS. 3a and 3b. The excitation light and the cleavage light irradiated by the optical arrangement of the present invention may be of such polarization in this and every other embodiment of the present invention.

A person skilled in the art unambiguously derives from the above presented descriptions that the geometrical parameters of the used wiregrid are to be adapted to the excitation light and the cleavage light which is irradiated by the optical arrangement. For example, the condition that the aperture of the wire grid between the wires should be smaller than the optical resolution at the pertinent wavelength, i.e. aperture<<optical resolution~λ/2 NA. In the context of the following figures, the apertures are termed slit-like openings.

The use of the wiregrid substrate of the presented device provides for an extreme optical confinement. In combination with a fast photochemical cleavage, which is used to decouple the so-called blocking moiety on the nucleotide to prevent continuation of the incorporation of the next nucleotide, the indicated advantages are realized. The use of the wiregrid has the additional advantage of being largely independent on the angle in incidence. Therefore, it can be used in combination with focussed beams to achieve a high intensity locally while keeping the rest in the dark. In other words, the wiregrid allows to excite and be sensitive to only those molecules, for example DNA fragments, that are very close to the surface in the evanescent field and thus no detection or effect on any label nucleotide outside the evanescent field is caused. For example, the evanescent field may elongate about 20 manometers from the first surface of the substrate. This may be the case for both the excitation light and the cleavage light.

A wiregrid substrate comprises a second surface opposite of the first surface and the optical arrangement is configured to irradiate the second surface of the substrate with the excitation light and the cleavage light. In other words, the substrates in the optical arrangement are positioned relative to each other such that the cleavage light and the excitation light are directly directed towards the second surface of the substrate. This may be seen as a backwards radiation of the substrate. On the front surface, the first surface, the regular wire structure is presented by the wiregrid. Between the regular metal wire, i.e. in the spaces between the wiregrid, the molecule, for example DNA fragments, is bound or immobilized.

The term "excitation light" in the context of the present invention applies to the wavelength $\lambda_{Ex1}$, $\lambda_{Ex2}$, $\lambda_{Ex3}$ and $\lambda_{Ex4}$, respectively. Consequently, for all four excitation wavelengths the substrate ensures that confinement and a creation of an evanescent wave of the respective light are generated. If desired, more or less light sources and/or fluorescent labels can be used without departing from the present invention.

According to another exemplary embodiment of the invention, the cleaving reaction takes a time $t_{cleavage}$, which depends on an intensity of the irradiated cleavage light. Furthermore, the incorporation of a second nucleotide into the bound molecule takes a time $t_{incorporation}$. The herein presented device comprises an optical arrangement which is configured and adjusted to provide the irradiated cleavage light with an intensity such that $t_{cleavage} < t_{incorporation}$.

Photo cleavage should only occur in those molecules which are incorporated already and bound to the surface. Reaction in the bulk would lead to unblocked reagents which could be built in without noticing and in this way introduce errors in the sequencing results. Therefore, it is valuable to only illuminate locally for a short period to make the cleavage reaction fast compared to the rate of incorporation of nucleotides by the enzyme. Working principle of the enzyme and the blocking moiety has been already described above. That disclosure applies within the herein described exemplary embodiment. The presented embodiments allow for synchronizing incorporation of the next nucleotides and ensure that the detected fluorescent signal is highly reliable.

The fact that the cleavage light is in an evanescent mode with respect to the substrate provides for the advantage that a repeated exposure does not lead to fluorescent labels in the solution which are bleached and which loose their function. In other words, the presented embodiment avoids such a bleaching and function-loosing of fluorescent labels in solution.

For an improved synchronization of the incorporation of several nucleotides at several bound molecules, the unblocking step with the cleavage light should be carried out as fast as possible, i.e. with the highest cleavage light intensity possible. This may be achieved by focussing the cleavage light, preferably the UV light, with a lens and scanning the surface by moving the lens or the substrate. The unblocking step may be carried out after reading the sequencing step. This reading can be carried out by scanning a focus beam or step and scan with field illumination. It may also be possible to embody cleavage light as a single flash of, for example, UV light for the total surface. In view of the reaction rate for the base incorporation for the sequencing reaction, the local cleavage light illumination time should be, for example, below 1 minute.

According to another exemplary embodiment, the substrate comprises several adjacent binding positions for binding molecules for the first surface along a first direction. The device is further configured to perform an optical scan by moving the substrate and the optical arrangement relative to each other along the first direction. Furthermore, the device is configured to perform the optical scan such that each binding position is firstly irradiated with the excitation light of at least the first wavelength $\lambda_{Ex1}$ and subsequently and secondly is irradiated with the cleavage light of the cleavage wavelength $\lambda_{CL}$ in a movement along the first direction.

In other words, a coupling of the cleavage light and the excitation light is presented which provides additional benefit of simultaneously reading-out the fluorescent signals and using the cleavage reaction, such that further nucleotides may be incorporated. This is done in a scanning mode that may provide for high local intensity of the used electromagnetic radiation without having the need of high power light source. In this arrangement, focussed light beams of the cleavage light and of the excitation light is useful. Therein the unblocking step may be carried out after the reading the sequencing step. In a preferred embodiment, the read-scanning can be coupled to the unblocking scanning by integrating both light beams in a single actuator. Furthermore, if desired, even a single lens might be used aligning the two light beams. Alternative two lenses can be integrated in a single stage or two separate stages can operate synchronously. This can also be implemented in the step and scan read approach, in which the cleavage step is also carried out in a step and scan mode by irradiating the same region as the excitation light source.

If desired, the presented device is configured to form such an optical scan in one continuous movement along the substrate. Therein a repeated continuous scanning is allowed. Thus the device is configured to firstly read-out whether the first nucleotide is incorporated into the molecule, e.g. a DNA fragment, or not and secondly is configured to cause the photochemical cleavage reaction at the previously read-out nucleotide in case it is incorporated into the molecule.

According to another exemplary embodiment of the invention, a method for optically controlling of DNA sequencing, in particular for optically controlling an iterative stepwise reaction to determine a sequence of nucleic acid by synthesis is presented. The method comprises the steps of providing a substrate with a molecule bound on a first surface of the substrate, irradiating the substrate with the excitation light of at least a first excitation wavelength $\lambda_{Ex1}$ by an optical arrangement and thereby optically exciting a fluorescent label of a first nucleotide which is incorporated in the bound molecule on the substrate. The method further comprises the step of confining the excitation light by the substrate thereby providing for an evanescent wave of the cleavage light by the substrate of the first surface of the substrate. As a further step, the method defines receiving and detecting fluorescence of the excited fluorescent label of the first incorporated nucleotide by the optical arrangement. Furthermore, irradiating the substrate with cleavage light of the cleavage wavelength $\lambda_{CL}$, preferably UV light, by the optical arrangement and thereby optically inducing a photochemical cleaving reaction at the first incorporated nucleotide is further comprised. A method further defines the step of confining the cleavage light of the cleavage wavelength $\lambda_{CL}$ by the substrate thereby providing for an evanescent wave of the cleavage light by the substrate at the first surface of the substrate.

The blocking moiety and the fluorescent labels may be cleaved away simultaneously, e.g. in case the blocking moiety comprises the fluorescent label, or may also be cleaved away in different steps.

In other words, the presented method provides for a surface selective irradiation of excitation light and of a surface selective irradiation of cleavage light. Consequently, the presented method ensures that only fluorescent label incorporated in nucleotides which are incorporated in molecules bound to the first surface of the substrate, are optically excited to emit a fluorescent signal. Such fluorescent signal of only fluorescent label close the first surface are then detected by the optical arrangement. This enhances the quality of the received and detected fluorescence signal. Additionally, the presented method ensures that only fluorescent labels are cleaved away from nucleotides, which are incorporated in molecules bound to the first surface of the substrate. Herein, a degradation of the solution, or of a moiety comprised therein, which solution is comprised by the device, can be avoided. In other words, the effective concentration of nucleotides which can be used for the process of synthesis is not unintentionally decreased.

Thus, the presented method avoids that fluorescent labels in the solution are bleached out and loose their function. This may further reduce the costs of a process of determining a sequence of a nucleic acid like for example a DNA sequencing.

According to another exemplary embodiment of the invention, a program element for optically controlling a DNA sequencing, in particular for optically controlling an iterative stepwise reaction to determine a sequence of a nucleic acid by synthesis, which, when being executed by a process, be adapted to carry out, irradiating a substrate with excitation light of at least a first excitation wavelength $\lambda_{Ex1}$ by an optical arrangement and thereby optically exciting a fluorescent label of a first nucleotide which is incorporated into a molecule bound on a first surface of the substrate, confining the excitation light by the substrate thereby providing for an evanescent wave of the excitation light by the substrate at the first surface of the substrate, receiving and detecting fluorescence of the excited fluorescent label of the first incorporated nucleotide by the optical arrangement, irradiating the substrate with cleavage light of a cleavage wavelength $\lambda_{CL}$, preferably UV light, by the optical arrangement and thereby optically inducing a photochemical cleaving reaction at the first incorporated nucleotide, and confining the cleavage light of the cleavage wavelength $\lambda_{CL}$ by the substrate thereby providing for an evanescent wave of the cleavage light by the substrate at the first surface of the substrate, is presented.

According to another exemplary embodiment of the invention, a computer-readable medium, on which a computer program for optically controlling a DNA sequencing, in particular for optically controlling an iterative stepwise reaction to determine a sequence of a nucleic acid by synthesis is stored, which, when being executed by a processor, is adapted to carry out irradiating a substrate with excitation light of at least a first excitation wavelength $\lambda_{Ex1}$ by an optical arrangement and thereby optically exciting a fluorescent label of a first nucleotide which is incorporated into a molecule bound on a first surface of the substrate, confining the excitation light by the substrate thereby providing for an evanescent wave of the excitation light by the substrate at the first surface of the substrate, receiving and detecting fluorescence of the excited fluorescent label of the first incorporated nucleotide by the optical arrangement, irradiating the substrate with cleavage light of a cleavage wavelength $\lambda_{CL}$, preferably UV light, by the optical arrangement and thereby optically inducing a photochemical cleaving reaction at the first incorporated nucleotide, and confining the cleavage light of the cleavage wavelength $\lambda_{CL}$ by the substrate thereby providing for an evanescent wave of the cleavage light by the substrate at the first surface of the substrate, is presented.

The computer program element may be part of a computer program, but it can also be an entire program by itself. For example, the computer program element may be used to update an already existing computer program to get to the present invention. The computer-readable medium may be seen as a storage medium, such as for example a USB stick, a CD, a DVD, a blue ray, a data storage device, a hard disk, or any other medium, on which a program element as described above can be stored.

It may be seen as a gist of the invention to provide for a new approach for determining a nucleic acid sequence. Thus sequencing can be carried out in a single fluid and in which no washing step is required. Based on strong confinement of firstly excitation light and secondly cleavage light due to a correspondingly configured substrate like for example wire-grid, the sequencing reaction can be read-out without washing the surface. Stepwise sequencing is achieved by using nucleotides with optically cleavable blocking moieties, that are attached to the nucleotides in the solution, that are to be incorporated in the molecules which are bound to the surface of the substrate. After a read-out with excitation light, which uses fluorescence, the built-in or incorporated nucleotides are unblocked by irradiating cleavage light through the same substrate. This ensures that only bound nucleotides are unblocked. In other words, the method and device of the present invention are configured to stepwise and optically induced incorporation of nucleotides with a sequence, which corresponds to a sequence of nucleotides of the bound molecule. Furthermore, the method and the device are configured to stepwise and optically read-out and determine the sequence of nucleotides which are incorporated in the bound molecules. Furthermore, the method and the device of the present invention are configured to base the determination of the sequence of the incorporated nucleotides on the received and detected respective fluorescence light emitted by the fluorescent label of the respective incorporated nucleotides.

According to another exemplary embodiment the use of a moiety as a blocking moiety in DNA sequencing is presented wherein the moiety is chosen from the group comprising a derivative of nitrophenylethyl, 5-methyl(2-(2-nitrophenyl)propyl) carbonate-dUTP analogue, 5-methyl(2-oxo-1,2-diphenylethyl) carbonate-dUTP analog, and any combination thereof.

Using the blocking moiety 5-methyl(2-(2-nitrophenyl) propyl) carbonate-dUTP analogues in DNA sequencing device has two advantages. Firstly, it gives defined, less reactive remnants after the photochemical cleavage resulting in a more clear process. Secondly, it has a high reaction rate. Compared to other photocleavable molecules, the new molecules are derivatives of the nitrophenylethyl moiety leading to nitrobenzen derived photoproducts that are much more stable than the nitros compounds generated by photochemistry of the nitrophenylmethyl derived molecules. Further more, generation of $CO_2$ is a driving force and clean way to efficiently increase the photochemical reaction speed. Another advantage of the use of said blocking moieties in DNA sequencing is demonstrated by the fact that the reaction is completed at very low cleavage light intensity. This means that the amount of energy needed per spot can be reduced in the DNA sequencing device. Numeral examples will be given later on in the context of FIG. 7 and FIG. 9.

These and other features of the invention will become apparent from and are elucidated with reference to the embodiments described hereinafter.

BRIEF DESCRIPTION OF THE DRAWINGS

Exemplary embodiments of the invention will be described in the following drawings.

In principle, identical or similar parts are provided with the same reference symbols in the figures.

DETAILED DESCRIPTION OF EMBODIMENTS

Figure 1:
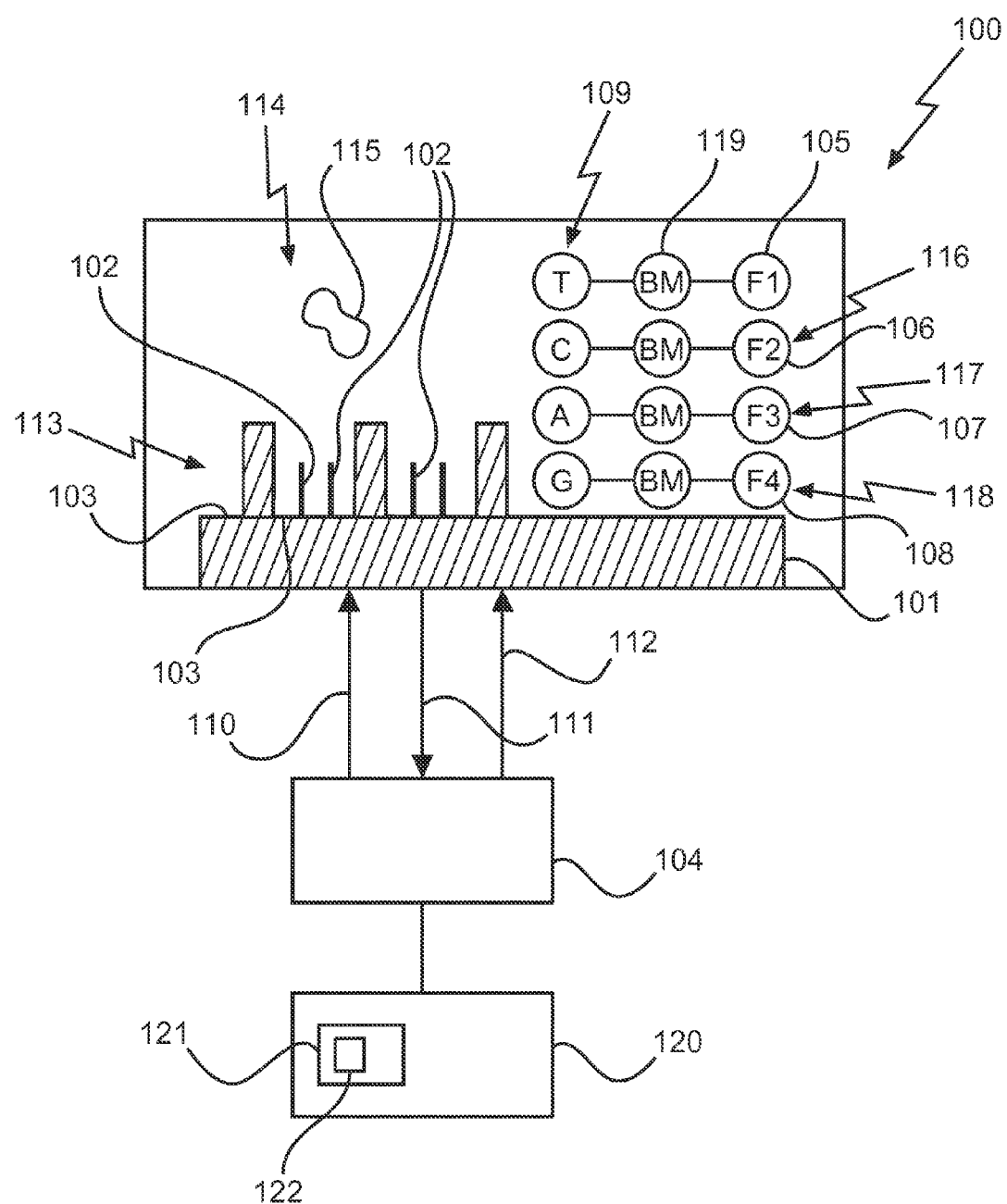
FIG. 1 schematically shows a device according to an exemplary embodiment of the invention.

FIG. 1 depicts a device 100 for optically controlling an iterative stepwise reaction to determine a sequence of a nucleic acid by synthesis. The device comprises a substrate 101 for binding at least one molecule 102 on the first surface 103 of the substrate. The molecule 102 which is bound on the first or front surface 103 of the substrate 101 can for example be a fragment of a DNA. Furthermore, the optical arrangement 104 is shown in FIG. 1. FIG. 1 schematically shows that the optical arrangement is configured to direct excitation light 110 of for example the first excitation wavelength $\lambda_{Ex1}$ to the substrate. Furthermore, four different nucleotides are schematically shown and are depicted with reference signs 109, 116, 117 and 118. For example, a first nucleotide 109 is shown as Thymine, T. The nucleotide 109 comprises a blocking moiety 119. Furthermore, the blocking moiety 119 comprises the first fluorescent label 105. In an analog way, second nucleotide 116 is schematically depicted in FIG. 1, from which can be gathered that also a blocking moiety 119 and the second fluorescent label 106 is comprised. The third nucleotide 117 comprises also a blocking moiety and a third fluorescent label 107. Additionally, the fourth nucleotide 118 is schematically depicted which comprises also a blocking moiety and a fourth fluorescent label 108. However, sample 114 may comprise a much larger plurality of such nucleotides, and nucleotides 109, 116, 117 and 118 are shown here merely as a symbolic depiction. Furthermore, FIG. 1 shows a solution 114 in which the nucleotides and the enzyme 115 are comprised. In case one of the shown four nucleotides is incorporated in the bound molecule 102, the presented device 100 provides for the following advantages. The optical arrangement is configured to receive and detect fluorescence light emitted by the fluorescent label of the first nucleotide incorporated into the bound molecule 102.

As can further be gathered from FIG. 1, the optical arrangement is configured to direct cleavage light 112 of cleavage wavelength $\lambda_{CL}$ to the substrate. This allows to optically induce a photochemical cleavage reaction at the first incorporated nucleotide to cleave the respective fluorescence wave from the first incorporated nucleotide. Furthermore, the substrate 101 is configured to confine excitation light such that an evanescent wave of the excitation light at the first surface of the substrate is created. Moreover, the substrate is configured to confine also the cleavage light such that an evanescent wave of the cleavage light as the first surface of the substrate is created. This may also be seen in FIGS. 3a and 3b. In the embodiment of FIG. 1, the substrate is configured as a wiregrid 113 for the excitation light 110 and for the cleavage light 112. Therefore, the wiregrid 113 comprises a regular pattern, like for example a regular metal wire structure. As can be gathered from FIG. 1, slit-like openings are provided between the regular patterns, in which openings the bound molecules 102 are immobilized at the first surface 103 of the substrate 101. Furthermore, FIG. 1 depicts a processing unit 120 which comprises a computer-readable medium 121 on which a computer program element 122 is stored. Said program element 122 is adapted to instruct the processing unit 120 to further instruct the device 100 to perform the above and below described method for optically controlling an iterative stepwise reaction to determine a sequence of a nucleic acid by synthesis. The device 100 of FIG. 1 is configured to stepwise and optically induce the incorporation of nucleotides 109, 116, 117, 119 with a sequence, which is complementary to the sequence of nucleotides of the bound molecule 102. In case the molecule 102 is a DNA fragment, the nucleotides comprised by the sample 114 are incorporated into molecule 102 in a sequence that corresponds to the nucleotide sequence of molecule 102.

The device is further configured to base the determination of the sequence of the incorporated nucleotides on the received and detected response fluorescence light emitted by the fluorescent label of the respective incorporated nucleotide. Therefore, the presented device 100 of FIG. 1 firstly ensures that only nucleotides are read-out by the excitation light 110, which nucleotides are incorporated into a bound molecule 102 by the use of an evanescent wave of the excitation light. Secondly, the device 100 of FIG. 1 ensures that only bound nucleotides will be unblocked by the cleavage light which avoids unblocking of nucleotides that are not yet contained i.e. incorporated by the molecule 102. Consequently, the detected fluorescence signal 100 may be seen as the light 111, is highly reliable for the determination of the sequence of the nucleic acids.

Consequently, the cost and speed of the DNA sequencing performed with the device 100 of FIG. 1 are both improved. Less fluid is necessary as no washing step is needed. The device of FIG. 1 shows a simplification and cost reduction of sequencing. The presented device 100 of FIG. 1 allows for a new process combination by allowing an assemble-based easy read-out without any washing step, meaning a single reagent filling for all reads. The blocking moieties used within the exemplary nucleotides 109, 116, 117, 118 may for example be a photo-cleavable 3'-unblocked reversible terminator. However, also other blocking moieties, using for example steric hindering, may be used to reach the desired and above described effects.

Furthermore, the optical arrangement 104 as shown in FIG. 1 may be configured to provide the irradiated cleavage light with an intensity such that the cleaving reaction time $t_{cleavage}$ is smaller than the time it takes to incorporate the second nucleotide into the molecule 102. As the cleaving reaction time $t_{cleavage}$ depends on the intensity of the irradiated cleavage light, FIG. 1 may provide for a selected combination of nucleotides with a specific blocking moiety and a configuration of the optical arrangement regarding the intensity of the cleavage light. In other words, the intensity of the cleavage light of the device of FIG. 1 is adapted such that for the used combination of nucleotides and blocking moieties the cleaving reaction time $t_{cleavage}$ is smaller than $t_{incorporation}$.

If desired, additionally or alternatively, the following set-up of device 100 may be provided to the user. The residence may be seen as an average residence time and in the spot of cleavage light of a non-incorporated nucleotide. An optical arrangement may further be configured to provide the irradiated cleavage light with an intensity such that $t_{cleavage}$ is smaller than $t_{residence}$. Consequently, no degradation of free and unbound nucleotides due to an undesired cleavage reaction happens. Thus, by configuring the device such that $t_{cleavage}$ is smaller than $t_{residence}$ the probability that a non-incorporated nucleotide is affected by cleaving is reduced or eliminated. In other words, to avoid cleavage reactions in the bulk the average residence time of the molecules in the evanescent field of the wiregrid should be smaller or much smaller than the reaction time required for cleavage at the pertinent intensity. With a depth of the evanescent field of the order of 25 nm or less and a diffusion coefficient of the nucleotide of the order of 1e-10 m2/s the time it takes for the molecule to diffuse in and out the evanescent field can be estimated as: (5e-8 m)2/1e-10=25 microseconds. Depending on the illumination time required for unblocking the bound molecules the probability of damage can be derived. Assume an illumination time of 0.1 s this would be 1:4000, with an illumination time of 10 ms it would be 1:400, etc.

Likewise the total damage is proportional to the volume fraction in the evanescent field over the total volume of reagent solution. With a chamber height of 100 µm the ratio is 1:4000. This means that in the worst case of damaging all molecules in the evanescent field only 0.025% of the molecules will be damaged. With a read length of 100 finally 2.5% of the molecules in solution would be damaged (worst case) which is still acceptable from a sequencing point of view.

Figure 2:
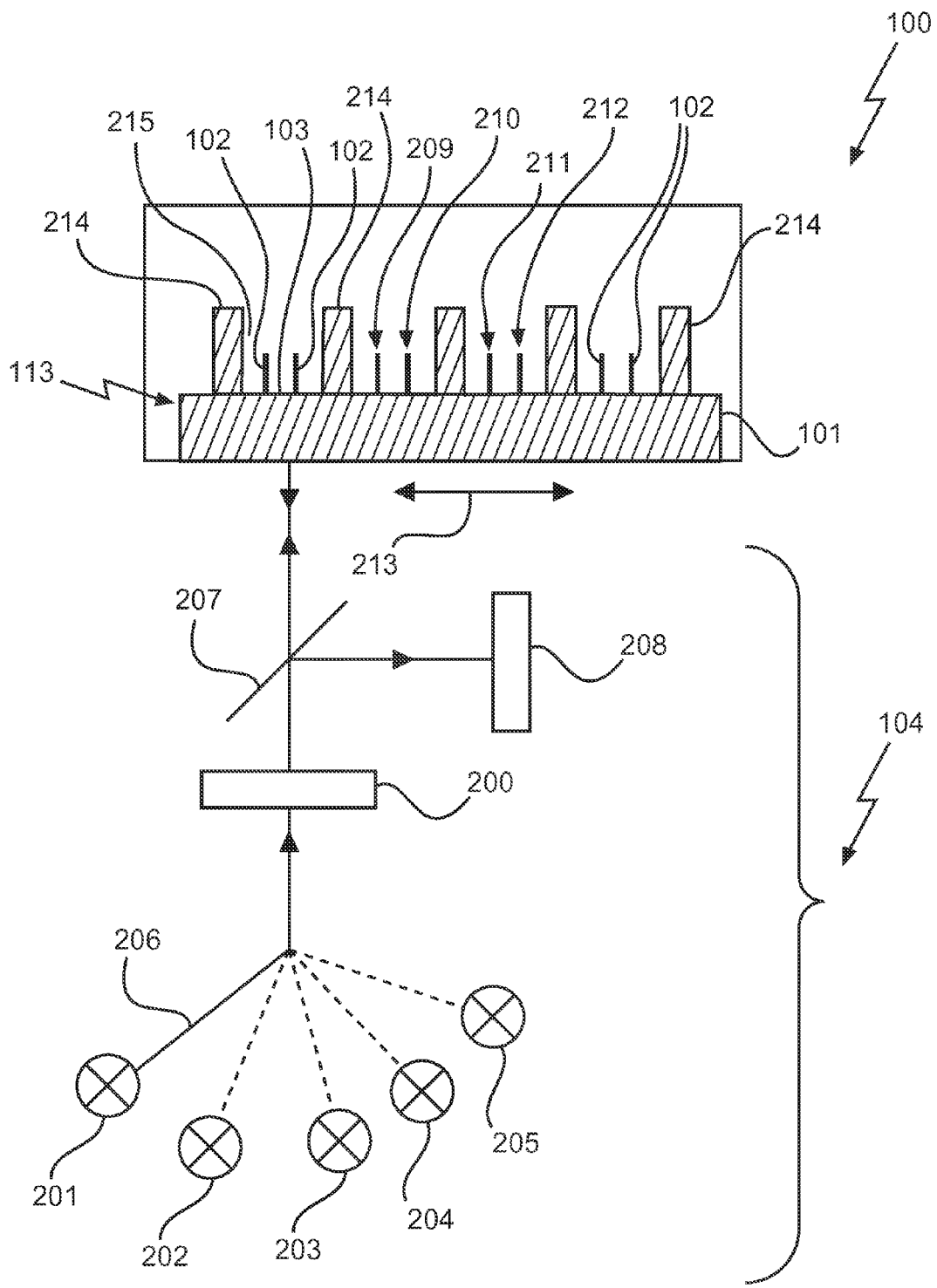
FIG. 2 schematically shows a device according to an exemplary embodiment of the invention.
Figure 4:
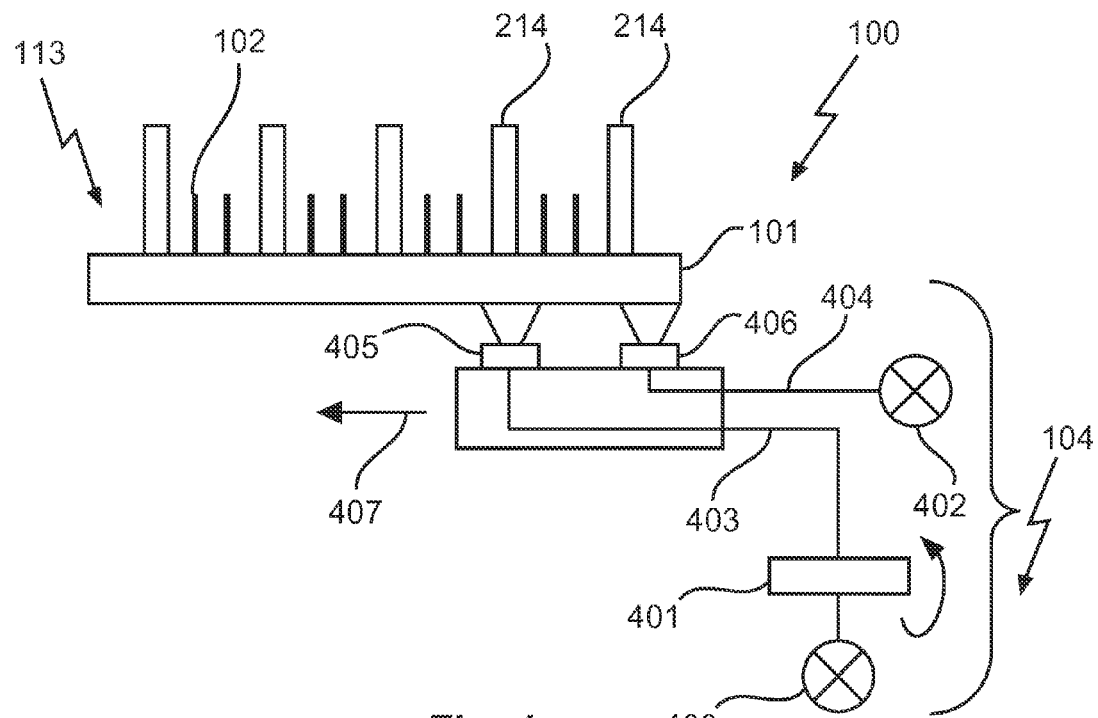
FIG. 4 schematically shows a device according to an exemplary embodiment of the invention.

In the following, information for using the device of FIG. 1, as well as the devices 100 of FIGS. 2 and 4 is provided. For an improved synchronization the unblocking step should be carried out as fast as possible, i.e. with the highest intensity possible. This can be achieved by focussing the UV-light with a lens and scanning the surface by moving the lens or the substrate. The unblocking step is carried out after reading the sequencing step. This reading can be carried out by scanning a focused beam or step-and-scan with field illumination. In a preferred embodiment the read scanning can be coupled to the unblocking scanning by integrating both light beams in a single actuator, possibly even in a single lens by aligning the light beams. Alternatively, two lenses can be integrated in a single stage or two separate stages can operate synchronously. This can also be implemented in the step and scan read approach, in which the UV-step is also carried out in a step and scan mode by illuminating the same field as the reader. The preferred embodiment will depend on the available UV light source and its power. One can also envision a single flash of UV for the total surface if enough power is available and/or the area of the sequencing surface is limited. In view of the reaction rate for the base incorporation for the sequencing reaction the local UV illumination time should be well below 1 minute.

FIG. 2 shows a device 100 which is configured to optically control an iterative stepwise reaction to determine a sequence of a nucleic acid by synthesis. Similar to FIG. 1, a wiregrid substrate 113 is shown on which a plurality of molecules 102 are immobilized, i.e. are bound. As can be seen from FIG. 2, a regular pattern 214 provides for slit-like openings 215 in which the molecules 202 are bound on the first surface 203. The substrate comprises several adjacent binding positions 209, 210, 211 and 212 for binding molecules to the first surface along a first direction 213. Said binding positions may be seen as spots which can be covered with clones of identical molecules, such that the optical signal, which is generated, can be increased. The substrate 101 then provides for an array of such spots, i.e. of such binding positions, with respectively different clones. This may enhance the throughput. Both devices 100 of FIGS. 1 and 2 allow a DNA sequencing with only one liquid, thereby avoiding the need to provide for washing steps in which the solution liquid is changed. Furthermore, the optical arrangement 104 comprises five different light sources 201 to 205. The light sources 201 to 204 may be seen as excitation light sources in order to provide for four different excitation wavelength $\lambda_{Ex1}$ to $\lambda_{Ex4}$ as described previously. The light source 205 provides for cleavage light with a wavelength $\lambda_{CL}$. For example, the light source 205 may emit UV light. Reference numeral 206 symbolically depicts a switching device which allows the optical arrangement 104 to switch between the five wavelengths $\lambda_{Ex1}$ to $\lambda_{Ex4}$ and $\lambda_{CL}$. Furthermore, the light emitted by at least one of said light sources 201 to 205 is directed towards the polarization filter 200. Furthermore, a dichroic mirror 207 is shown which transmits the emitted light of the light sources 201 to 205 towards the substrate 101. After a fluorescent label has been excited by an evanescent wave of excitation light (at least one of the wavelengths $\lambda_{Ex1}$ to $\lambda_{Ex4}$), the fluorescence photons emitted by the fluorescent label or labels are directed towards the dichroic mirror 207 and are directed towards fluorescence detector 208. As can be seen from FIG. 2, the optical arrangement 104 may be scanned along the direction 213. Consequently, the device 100 of FIG. 2 is configured to perform an optical scan by moving the substrate 101 and the optical arrangement 104 relative to each other along the first direction 213. Consequently, the device allows to perform the optical scan such that each binding position is firstly irradiated with the excitation light and subsequently and secondly is irradiated the cleavage light of the cleavage wavelength in a movement along the first direction 213, The unblocking step, using the cleavage light, can thus be carried out after reading the fluorescence of the excited incorporated nucleotides.

Figure 3A:
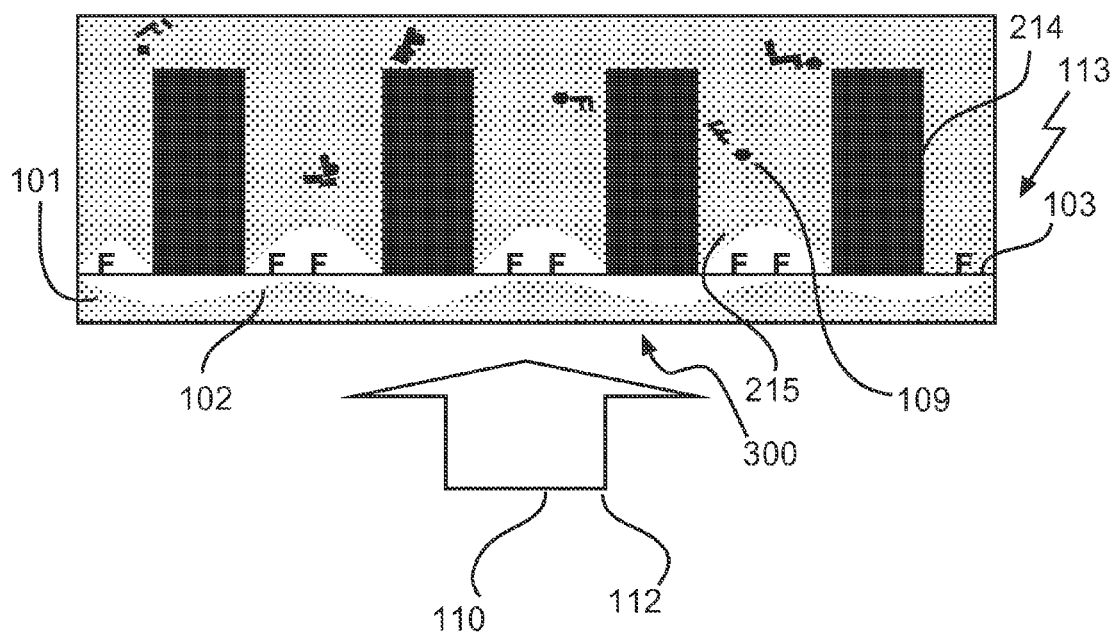
FIGS. 3a and 3b schematically show a substrate creating an evanescent wave in the region of the bound molecule used in an exemplary embodiment of the present invention.
Figure 3B:
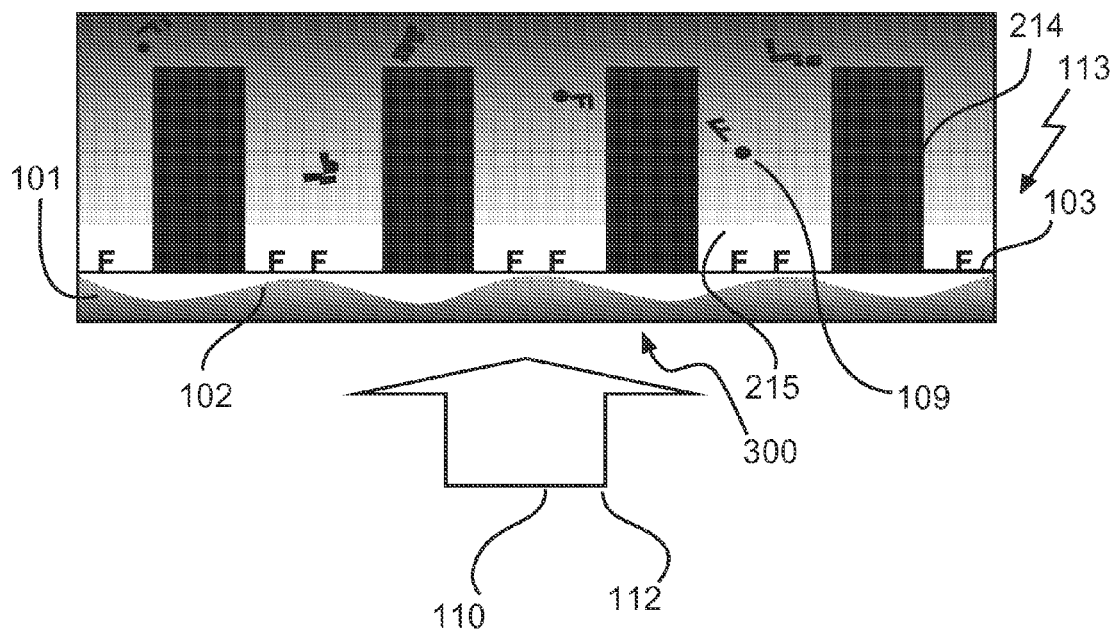

FIGS. 3a and 3b show a substrate 101 which is embodied as a wiregrid 113. Regular pattern 214, which may be embodied as a regular metal wire structure provides four slit-like openings 215, in which the molecules 102 are immobilized. As symbolized by the arrow, the excitation light 110 and the cleavage light 112 is directed to the substrate towards the second surface of the substrate. The second surface is opposite to the first surface 103 at which the molecules are bound. Consequently, the wiregrid is illuminated from the back. Furthermore, FIGS. 3a and 3b show that several unbounded nucleotides 109 are present in the solution which may later on be incorporated into the molecule 102 bound on the first surface. FIGS. 3a and 3b depict the evanescent wave 300 between the metal structures with dimensions smaller than the optical resolution at the wavelength of the light beam. The evanescent wave is depicted by FIG. 3b by brightness gradation which corresponds to field intensity gradation. FIG. 3b shows electromagnetic field strength for a wiregrid illuminated with TE polarized light. High brightness indicates a high intensity and a low brightness indicates a low intensity. The herein presented substrate can be exemplarily used in the devices of FIGS. 1 and 2 as well as in the device of FIG. 4. However, it should be noted that surface confinement by evanescent waves can be achieved in other ways, which the person skilled in the art knows.

Total internal reflection may also be used in order to provide the evanescent wave in this or in any other embodiment of the invention.

FIG. 4 shows a device 100 for continuously scanning the substrate 101. The device 100 provides for an optical arrangement 104 with a light source 400 for emitting excitation light. By means of a colour filter 401 which can be rotated different excitation wavelengths may be provided. Additionally, a cleavage light source 402 is provided. Light guiding members 403, 404 are presented in order to direct the light to the respective optical elements 405, 406. As can be seen, separate lenses and optical channels are used for the excitation light and for the cleavage light. However, if desired, it can also be combined with the optical paths of both light sources. The optical arrangement 104 shown in FIG. 4 allows for a relative movement between the substrate 101 and the optical arrangement 104 in the direction of 407.

FIG. 4 may also comprise a dichroic mirror configured to transmit excitation light and is configured to reflect the fluorescent light emitted by the used fluorescent labels. Furthermore, the substrate may be configured to transmit only a first polarization of light and is configured to reflect a second polarization of light which is perpendicular polarized to the first polarization. The polarization filter is configured to transmit only the first polarization of light. The device of FIG. 4 is configured to generate data which describes the sequences of the nucleic acids that were incorporated into the bound molecule based on the optically stepwise action that is controlled optically by the device.

Figure 5:
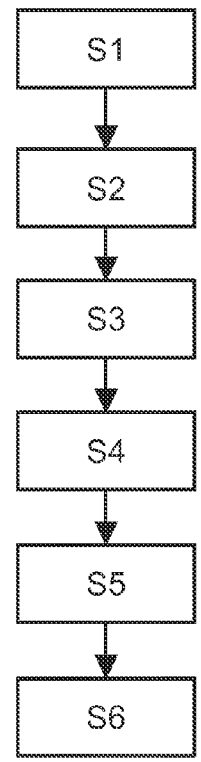
FIG. 5 shows a flow diagram of a method according to an exemplary embodiment of the invention.

FIG. 5 shows a flow diagram of a method for optically controlling an iterative stepwise reaction to determine a sequence of a nucleic acid by synthesis. The method comprises the step of providing a substrate with a molecule bound on a first surface of the substrate in step S1. By irradiating the substrate with excitation light of at least first excitation wavelength $\lambda_{Ex1}$ by an optical arrangement and thereby optically excited a fluorescent label of a first nucleotide which is incorporated in the bound molecule on the substrate, is shown with step S2. Furthermore, step S3 depicts the step of confining the excitation light by the substrate thereby providing for an evanescent wave of the cleavage light by the substrate at the first surface of the substrate. Receiving and detecting fluorescence of the excited fluorescent label of the first incorporated nucleotide by the optical arrangement is presented by step S4. Step S5 irradiating the substrate with cleavage light of the cleavage wavelength $\lambda_{CL}$, preferably UV light, by the optical arrangement and thereby optically inducing a photochemical cleaving reaction at the first incorporated nucleotide, is depicted with step S5. Furthermore, in step S6 confining the cleavage light of the cleavage wavelength $\lambda_{CL}$ by the substrate thereby providing evanescent wave of the cleavage light by the substrate at the first surface of the substrate is provided.

By repeating the presented method steps S1 to S6 the user is enabled to determine the sequence of nucleic acid that have been incorporated into a molecule bound to the first surface of the substrate. Consequently, after steps S1 to S6 the user may perform, if desired, the following steps. Incorporating a second nucleotide into the molecule bound at the first surface of the substrate; then blocking an activity of an enzyme by the second nucleotide after its incorporation the molecule. Irradiating the substrate with excitation light by the optical arrangement and thereby optically exciting the fluorescent label of the second incorporated nucleotide may be performed as well. Confining the excitation light by the substrate, thereby providing evanescent wave of the excitation light by the substrate at the first surface of the substrate is a further step of this secondary cycle. The step of receiving and detecting fluorescence of the excited fluorescent label of the second incorporated nucleotide may then be performed. Irradiating the substrate with cleavage light, preferably UV light, by the optical arrangement and thereby optically and using a photochemical cleaving reaction at the second incorporated nucleotide can be performed as well. As another step for confining the cleavage light by the substrate thereby providing for an evanescent wave of the cleavage light by the substrate at the first surface of the substrate is presented.

Figure 6:
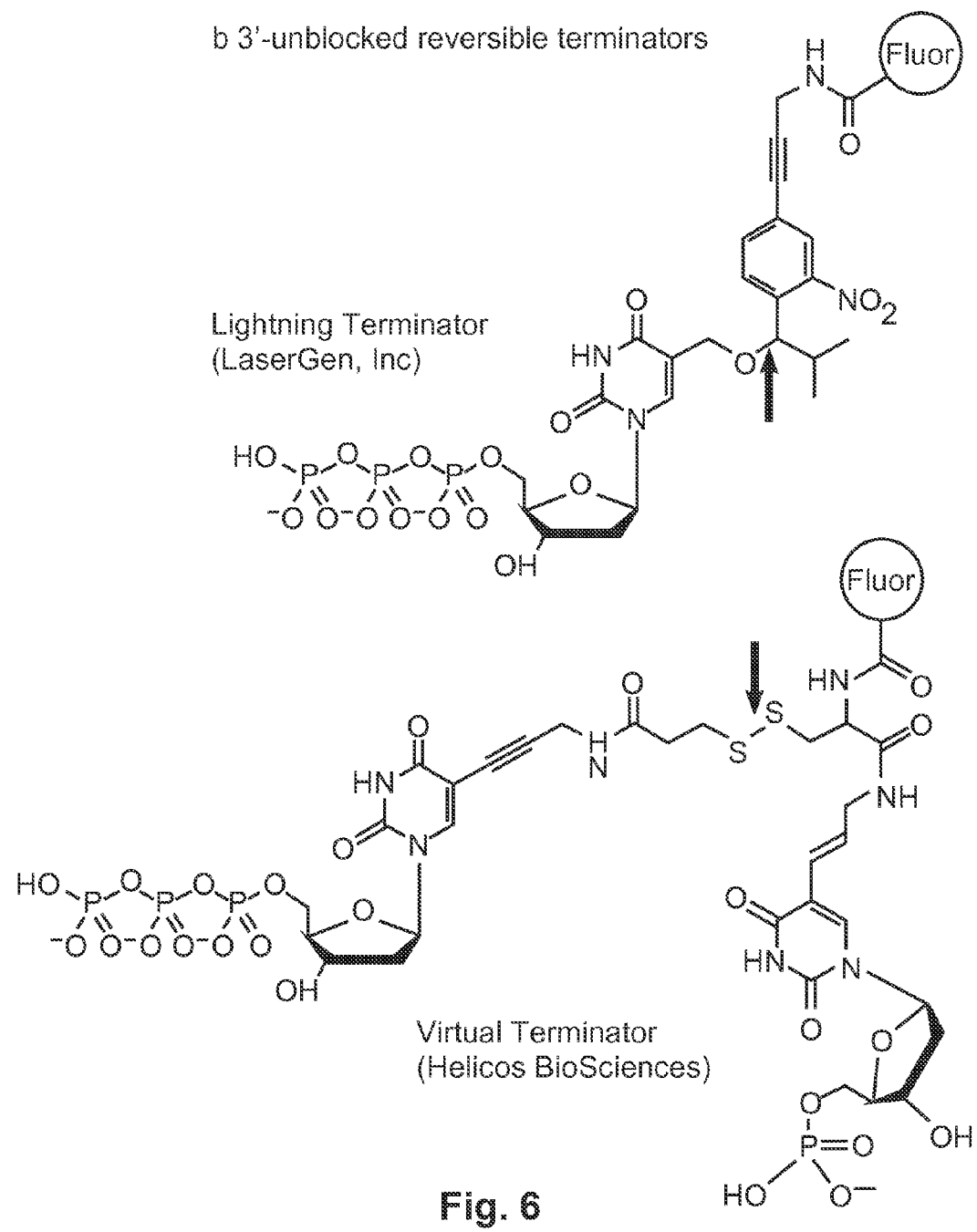
FIG. 6 schematically shows two blocking moieties.

FIG. 6 shows blocking moieties of "*Sequencing technologies, the next generation*" by Michael L. Metzker, Nature Genetics 11 (2010) 31. Firstly, by using a 3'-blocked reversible terminators and secondly by using a 3'-unblocked reversible terminators. The 2nd class is very interesting as in this case the 3' position of the ribose unit is unblocked and the in-corporation of the next nucleotide is prevented by the bulky group that also contains the fluorescent label attached to the base paring moiety at 5' position of the ribose unit as can be seen in FIG. 6.

Figure 8:
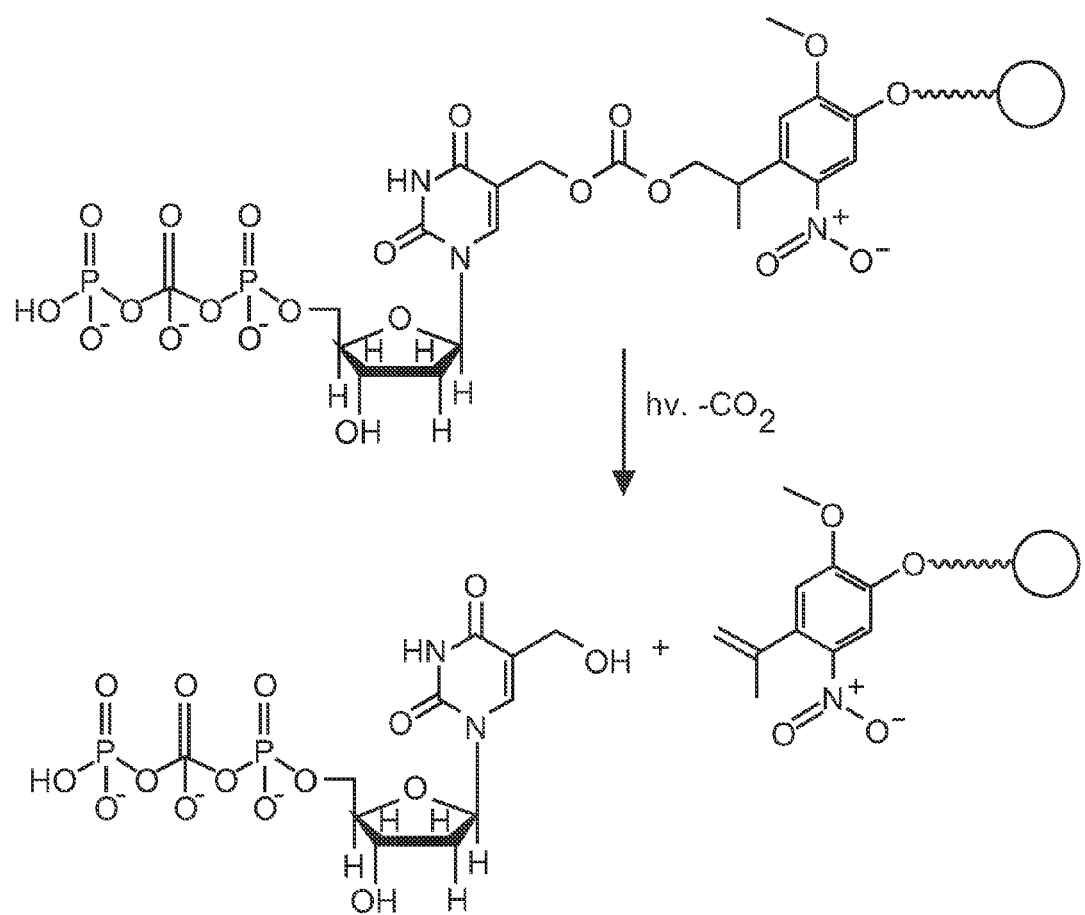
FIG. 8 schematically shows a photochemical cleavage process.

The present invention may use wiregrid technology and the un-blocking step is done with e.g. polarized UV light of 365 nm. Consequently, after this unblocking step the next labeled nucleotide is built in and detected by scanning the wiregrid using polarized light such that only the labeled nucleotides at the DNA fragment at the surface are detected. After this is done, again by providing an unblocking step using UV light the next labeled nucleotide can be built in and detected etc. For this process to work one may need: 1. A photo-cleavable 3'-unblocked reversible terminator, as with the 3' blocked variants the removal of the 3-blocking groups (—N3 or —CH2) have to be done in phase. 2. The photo-cleaving reaction should be faster than the incorporation of new nucleotides by the polymerase. The so-called 3'-OH unblocked terminators invented by Metzker et al, namely: 2-nitrobenzyl alkylated HOMedU tri-phosphates might be slow for this purpose compared to blocking moieties we present later on, see FIGS. 8 to 10.

Figure 7:
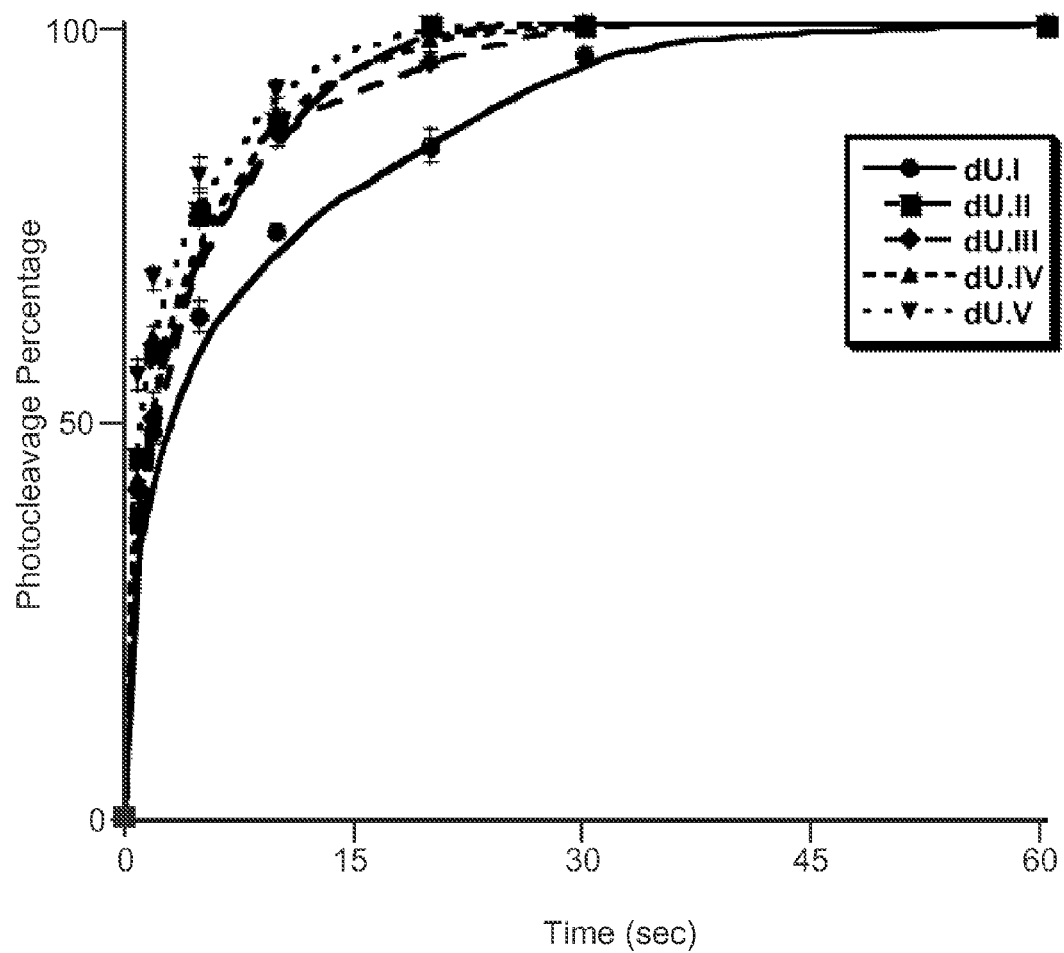
FIG. 7 schematically shows a time course plot of photochemical cleavage rates.

FIG. 7 shows a time course plot of photochemical cleavage rates of dU.I-dU.V incorporated into the BODIPY-FL labelled primer-1/oligoTemplate-4 complex using Terminator polymerase. FIG. 7 is taken from V. A. Litosh, W. Wu, B. P. Stupi, J. Wang, S. E. Morris, M. N. Hersh, and M. L. Metzker, "Improved nucleotide selectivity and termination of 3'-OH unblocked terminators by molecular tuning of 2-nitrobenzyl alkylated HOMedU triphosphates", Nucl. Acids Res, Vol 36, issue 6, 2011, E39. As can be clearly see from this FIG. 7 the time scale at which the photo-cleavage effect occurs is in the orders of 10 s. Or as concluded by these authors: "All 5-(2-nitrobenzyloxyyl)methyl-dUTP analogues were photo-chemically cleaved to 100% efficiency within 60 s at 365 nm UV light exposure with an intensity of ~0.7 W/cm$^2$ in azide solution". Importantly these authors also found that the Terminator polymerase continued to show good activity even after being exposed to 365 nm UV light for 150 min with intensities up to 1 W/cm2.

However this photo-cleave chemistry is slower to what we found with different blocking moieties we used. Our approach might improve the non-cycling reaction we propose. Note the light intensities needed for in the chemistry by Metzker et al is 1 W/cm2 which translates to 10 nW/(μm)2. We have used a chemistry using a moiety as a blocking moiety in DNA sequencing, wherein the moiety is a derivative of nitrophenylethyl. For example, 5-methyl(2-(2-nitrophenyl)propyl) carbonate-dUTP analogues, which have two advantages. First, it gives defined, less reactive remnants after the photochemical cleavage resulting in a more clear process. Second, it has a higher reaction rate as we have determined independently (see FIG. 9).

Figure 9:
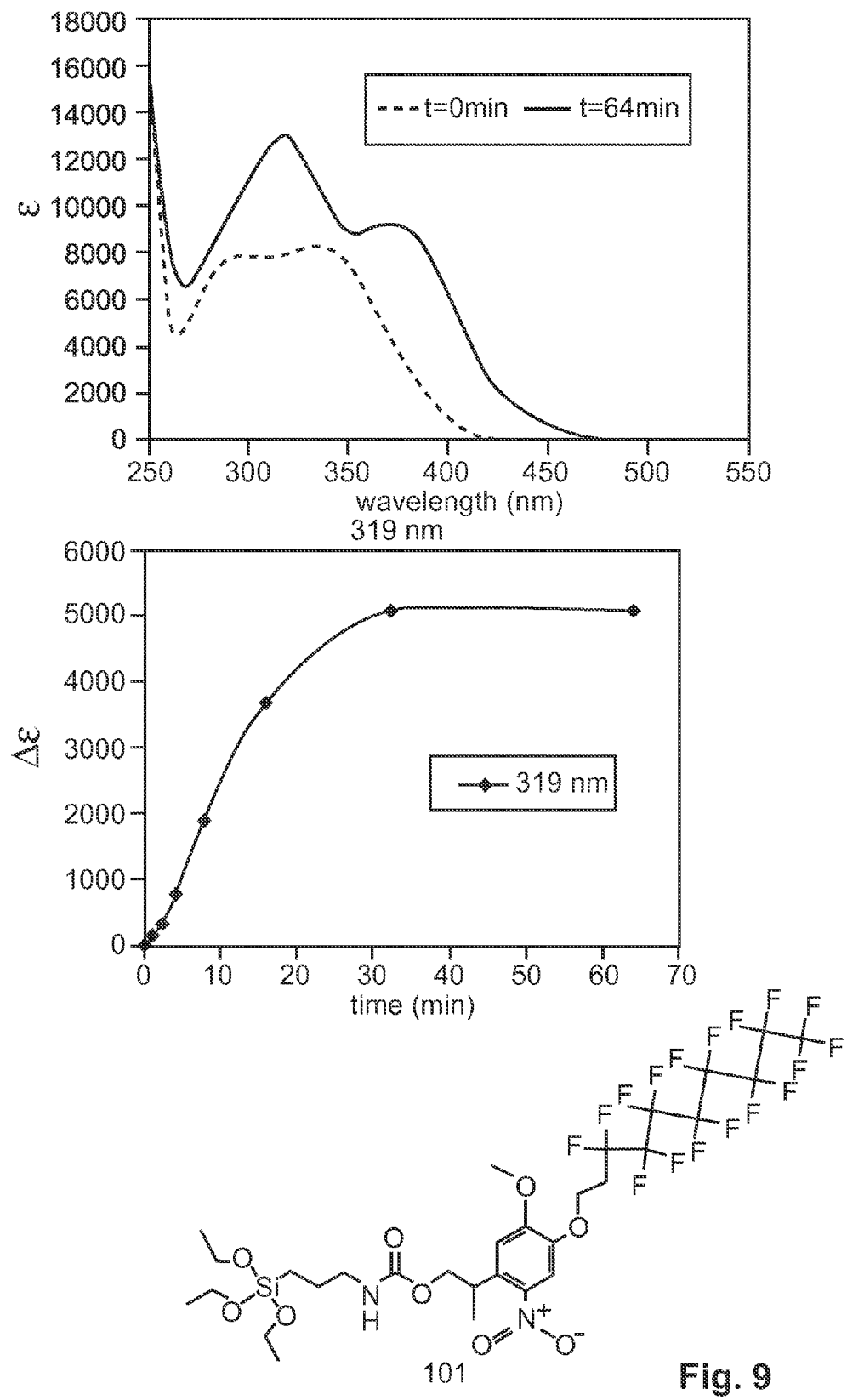
FIG. 9 schematically shows photo transformation graphs.

Compared to the photocleavable molecules described by Metzger, the new molecules are derivatives of the nitrophenylethyl moiety leading to nitrobenzen derived photoproducts that are much stable than the nitros compounds generated by photochemistry of the nitrophenylmethyl derived molecules of Metzger. Further more, generation of $CO_2$ is a driving force and clean way to efficiently increase the photochemical reaction speed. One further advantage of our chemistry is demonstrated by the fact that the photochemical cleavage reaction of compound 101 that is from a photochemical point of view very similar to the molecule of FIG. 8, completes within 30 minutes using a PL10 lamp at 10 cm which produces 4 mW/cm2. Compound 101 is depicted in FIG. 9 at the bottom. Also for the data see FIG. 9. Thus the reaction is completed slower as the example of the compounds of the reference cited above but, at 250× lower intensity. This means that the amount of energy needed per spot is 50 times lower.

FIG. 9 shows the efficiency of photo-transformation under 365 nm light of the compound 101 (our data). Note the spectra changes after 1 h of UV absorption blue to pink spectrum. B) Graph of the evolution of the photochemical reaction by the rise of the spectral peak at 319 nm as a function of excitation at 365 nm. Note that this data in ethanol shows that the evolution is complete after 30 min. (and for 80% complete after 20 min) by excitation with a PL10 lamp at 10 cm which is equivalent to an energy of 4 mW/cm2.

Figure 10:
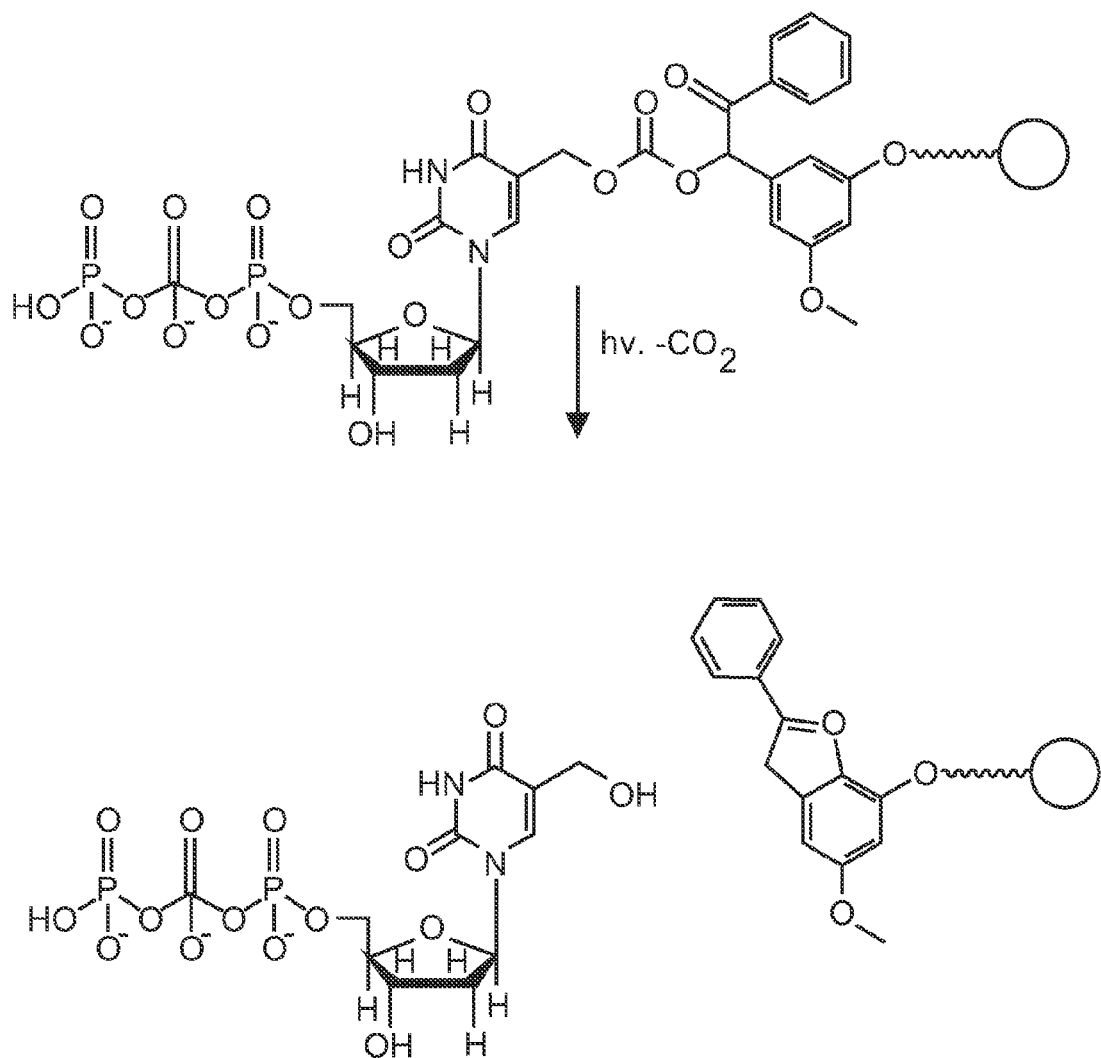
FIG. 10 shows a photochemical cleavage process of 5-methyl(2-oxo-1,2-diphenylethyl) carbonate-dUTP analogs used in an exemplary embodiment of the present invention.

A possible alternative for the nitro-compounds are the "5-methyl(2-oxo-1,2-diphenylethyl) carbonate-dUTP analogs" shown in FIG. 10 which exhibit also an efficient photochemical cleavage. They might also be used as a blocking moiety in any embodiment of the present invention, if desired.

Furthermore, the following compound may be used as blocking moiety according to the present invention:

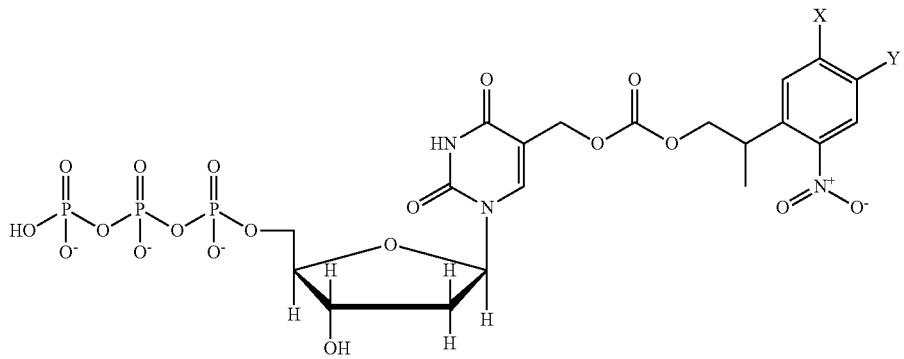

The following variations may also be used as blocking moiety according to the present invention: Compound 1 with: X=O(CH2)nZ with n=integer from 1 till 18 or X=O(C2H4O)nCH2Z with n=integer from 1 till 20 with Z=H or a linker connected to a fluorescent moiety and Y=(CH2)nA with n=integer from 0 till 18 or Y=O(CH2)nA with n=integer from 1 till 18 or O(C2H4O)nCH2A with n=integer from 1 till 20 with A=H or a linker connected to a fluorescent moiety, in such a combination that at least one of the groups A or Z have a linker connected to a fluorescent moiety.

Furthermore, the following compound may be used as blocking moiety according to the present invention:

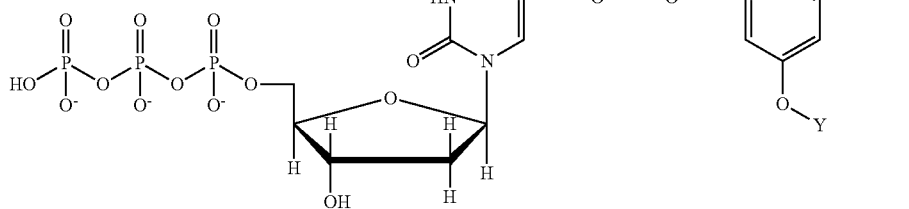

With X and Y are independently (CH2)nZ with n=integer from 1 till 18 or (C2H4O)nCH2Z with n=integer from 1 till 20 with Z=H or a linker connected to a fluorescent moiety in such combination that least one of the groups X or Y has a group Z that has a linker connected to a fluorescent moiety.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A device for optically controlling an iterative stepwise reaction to determine a sequence of a nucleic acid by synthesis, the device comprising:
    a substrate for binding at least one molecule on a first surface of the substrate,
    an optical arrangement,
    wherein the optical arrangement is configured to emit cleavage light of a cleavage wavelength $\lambda_{CL}$, wherein the cleavage light is polarized light,
    wherein the optical arrangement is configured to direct excitation light of at least a first excitation wavelength $\lambda_{EX1}$ to the substrate to excite a fluorescent label of a first nucleotide,
    wherein the first nucleotide is incorporated into the molecule bound on the first surface of the substrate,
    wherein the optical arrangement is configured to receive and detect fluorescent light emitted by the fluorescent label of the first nucleotide,
    wherein the optical arrangement is configured to direct the cleavage light of the cleavage wavelength $\lambda_{CL}$ to the substrate to optically induce a cleavage reaction at the first nucleotide to cleave a blocking moiety and the fluorescent label away from the first nucleotide,
    wherein the substrate is configured to confine the excitation light, wherein the substrate is configured to provide for an evanescent wave of the excitation light at the first surface of the substrate, wherein the substrate is configured to confine the cleavage light, wherein the substrate is configured to provide for an evanescent wave of the cleavage light at the first surface of the substrate, wherein the evanescent wave of the cleavage light induces the cleavage reaction, and wherein the substrate comprises a wiregrid including wires that are opaque.

2. The device according to claim 1, the device further comprising a solution with a plurality of nucleotides and an enzyme, wherein the nucleotides respectively comprise a blocking moiety, wherein the blocking moiety is configured to block a synthesizing activity of the enzyme when the respective nucleotide is incorporated into the molecule bound, to the first surface.

3. The device according to claim 2, wherein the blocking moiety is a photo cleavable 3'-unblocked reversible terminator.

4. The device according to claim 2, wherein the blocking moiety is chosen from the group comprising a derivative of nitrophenylethyl, 5-methyl(2-(2-nitrophenyl)propyl) carbonate-dUTP analogue, 5-methyl(2-oxo-1,2-diphenylethyl) carbonate-dUTP analog, and any combination thereof.

5. The device according to claim 1,
wherein the cleaving reaction takes a time $t_{cleavage}$,
wherein the cleaving reaction time $t_{cleavage}$ depends on an intensity of the irradiated cleavage light,
wherein incorporating a second nucleotide into the bound molecule takes a time $t_{incorporation}$, and
wherein the optical arrangement is configured to provide the irradiated cleavage light with an intensity such that $t_{cleavage} < t_{incorporation}$.

6. The device according to claim 1,
wherein the substrate comprises several adjacent binding positions for binding molecules to the first surface along a first direction,
wherein the device is configured to perform an optical scan by implementing a relative movement between the substrate and the optical arrangement along the first direction, and
wherein the device is configured to perform the optical scan such that each binding position is firstly irradiated with the excitation light of at least the first wavelength $\lambda_{Ex1}$ and subsequently and secondly irradiated with the cleavage light of the cleavage wavelength $\lambda_{CL}$ in a movement along the first direction.

7. The device according to claim 1, wherein the device is configured to stepwise and optically induce the incorporation into the bound molecule of nucleotides with a sequence, which is complementary to a sequence of nucleotides of the bound molecule, wherein the device is configured to stepwise and optically read out and determine the sequence of nucleotides which are incorporated into the bound molecule, and wherein the device is configured to base the determination of the sequence of the incorporated nucleotides on the received and detected respective fluorescent light emitted by the fluorescent label of the respective incorporated nucleotide.

8. The device according to claim 1, wherein the wiregrid forms slit-apertures, wherein each of the slit-apertures has a size that is less than $\lambda_{CL}/2NA$, and wherein NA is the numerical aperture of the respective aperture.

9. The device according to claim 1, wherein the wiregrid forms a plurality of apertures and wherein the at least one molecule is disposed within at least one of said apertures during the cleavage reaction.

10. The device of claim 9 wherein the plurality of apertures are slit-apertures, wherein each of the slit-apertures have a size that is less than $\lambda_{CL}/2NA$, and wherein NA is the numerical aperture of the respective slit-aperture.

11. The device of claim 1, wherein the wiregrid is configured reflect the cleavage light and to transmit light having a polarization that is different from a polarization of the cleavage light.

12. A method for optically controlling an iterative stepwise reaction to determine a sequence of a nucleic acid by synthesis, the method comprising the steps:

providing a substrate with a molecule bound on a first surface of the substrate, irradiating the substrate with excitation light of at least a first excitation wavelength $\lambda_{Ex1}$ by an optical arrangement and thereby optically exciting a fluorescent label of a first nucleotide, wherein the first nucleotide is incorporated in the bound molecule on the substrate, confining the excitation light by the substrate thereby providing for an evanescent wave of the cleavage light by the substrate at the first surface of the substrate, receiving and detecting fluorescence of the excited fluorescent label of the first nucleotide by the optical arrangement, irradiating the substrate with cleavage light of a cleavage wavelength $\lambda_{CL}$ by the optical arrangement and thereby optically inducing a cleaving reaction at the first nucleotide, wherein the cleavage light is polarized light, and confining the cleavage light of the cleavage wavelength $\lambda_{CL}$ by the substrate thereby providing for an evanescent wave of the cleavage light by the substrate at the first surface of the substrate, wherein the evanescent wave of the cleavage light induces the cleavage reaction and wherein the substrate comprises a wiregrid including wires that are opaque.

13. The method according to claim 12, the method further comprising the steps:

providing for a solution with a plurality of nucleotides and an enzyme, wherein the nucleotides respectively comprise a blocking moiety which comprises the fluorescent label, blocking a synthesizing activity of the enzyme by the blocking moiety when the respective nucleotide is incorporated into the molecule bound to the first surface, and wherein the step of inducing the cleaving reaction is performed such that the blocking moiety comprising the fluorescent label is cleaved away from the incorporated nucleotide.

14. The method according to claim 12, wherein the blocking moiety is chosen from the group comprising a derivative of nitrophenylethyl, 5-methyl(2-(2-nitrophenyl)propyl)carbonate-dUTP analogue, 5-methyl(2-oxo-1,2-diphenylethyl)carbonate-dUTP analog, and any combination thereof.

15. The method according to claim 12, wherein the substrate comprises several adjacent molecule binding positions at which a molecule is respectively bound to the first surface along a first direction, the method further comprising the steps:
performing an optical scan by implementing a relative movement between the substrate and the optical arrangement along the first direction, and performing the optical scan such that each bound molecule is firstly irradiated with the excitation light of at least the first excitation wavelength $\lambda_{Ex1}$ and subsequently irradiated with the cleavage light of the cleavage wavelength $\lambda_{CL}$ in a movement along the first direction.

16. The method according to claim 15,
wherein the cleaving reaction takes a time $t_{cleavage}$,
wherein the cleaving reaction time $t_{cleavage}$ depends on an intensity of the irradiated cleavage light, the method further comprising the step:
incorporating a second nucleotide into the bound DNA molecule, wherein the incorporation takes a time $t_{incorporation}$, and
selecting the intensity of the irradiated cleavage light at the optical arrangement such that $t_{cleavage} < t_{incorporation}$.

17. A program element for optically controlling an iterative stepwise reaction to determine a sequence of a nucleic acid by synthesis according to the method of claim 12, which, when being executed by a processor, is adapted to carry out:
   irradiating a substrate with excitation light of at least a first excitation wavelength $\lambda_{Ex1}$ by an optical arrangement and thereby optically exciting a fluorescent label of a first nucleotide, wherein the first nucleotide is incorporated into a molecule bound on a first surface of the substrate,
   confining the excitation light by the substrate thereby providing for an evanescent wave of the excitation light by the substrate at the first surface of the substrate,
   receiving and detecting fluorescence of the excited fluorescent label of the first nucleotide by the optical arrangement,
   irradiating the substrate with cleavage light of a cleavage wavelength $\lambda_{CL}$ by the optical arrangement and thereby optically inducing a cleaving reaction at the first incorporated nucleotide, and
   confining the cleavage light of the cleavage wavelength $\lambda_{CL}$ by the substrate thereby providing for an evanescent wave of the cleavage light by the substrate at the first surface of the substrate, wherein the evanescent wave of the cleavage light induces the cleavage reaction.

18. A computer-readable medium, on which a computer program for optically controlling an iterative stepwise reaction to determine a sequence of a nucleic acid by synthesis according to the method of claim 12 is stored, which, when being executed by a processor, is adapted to carry out:
   irradiating a substrate with excitation light of at least a first excitation wavelength $\lambda_{Ex1}$ by an optical arrangement and thereby optically exciting a fluorescent label of a first nucleotide, wherein the first nucleotide is incorporated into a molecule bound on a first surface of the substrate,
   confining the excitation light by the substrate thereby providing for an evanescent wave of the excitation light by the substrate at the first surface of the substrate
   receiving and detecting fluorescence of the excited fluorescent label of the first nucleotide by the optical arrangement,
   irradiating the substrate with cleavage light of a cleavage wavelength $\lambda_{CL}$ by the optical arrangement and thereby optically inducing a cleaving reaction at the first incorporated nucleotide, and
   confining the cleavage light of the cleavage wavelength $\lambda_{CL}$ by the substrate thereby providing for an evanescent wave of the cleavage light by the substrate at the first surface of the substrate, wherein the evanescent wave of the cleavage light induces the cleavage reaction.

* * * * *